(12) United States Patent
Schmidmaier et al.

(10) Patent No.: US 6,998,134 B2
(45) Date of Patent: Feb. 14, 2006

(54) BIOLOGICALLY ACTIVE IMPLANTS

(76) Inventors: Gerhard Schmidmaier, D-10557 Claudiusstrasse 12, Berlin (DE); Michael Raschke, D-12205 Weddingen Weg 31, Berlin (DE); Axel Stemberger, D-85579 Cramer-Klett-Strasse 35e, Neubiberg (DE)

( * ) Notice: Subject to any disclaimer, the term of this patent is extended or adjusted under 35 U.S.C. 154(b) by 441 days.

(21) Appl. No.: 09/801,752

(22) Filed: Mar. 9, 2001

(65) Prior Publication Data

US 2001/0031274 A1    Oct. 18, 2001

Related U.S. Application Data

(63) Continuation of application No. PCT/EP99/06708, filed on Sep. 10, 1999.

(30) Foreign Application Priority Data

Sep. 11, 1998    (DE) ............................... 198 43 251

(51) Int. Cl.
 *A61F 13/00*    (2006.01)
 *A61F 2/00*    (2006.01)

(52) U.S. Cl. ........................... 424/422; 424/423

(58) Field of Classification Search ............... 424/422, 424/423
 See application file for complete search history.

(56) References Cited

U.S. PATENT DOCUMENTS

| 4,338,926 | A |   | 7/1982 | Kummer et al. ......... 128/92 BC |
| 4,476,590 | A |   | 10/1984 | Scales et al. .................. 3/1.91 |
| 4,563,489 | A |   | 1/1986 | Urist ........................... 524/21 |
| 4,610,692 | A | * | 9/1986 | Eitenmuller et al. |
| 4,828,563 | A |   | 5/1989 | Müller-Lierheim .......... 623/16 |
| 4,902,515 | A |   | 2/1990 | Loomis et al. .............. 424/486 |
| 4,962,091 | A |   | 10/1990 | Eppstein et al. ............... 514/2 |
| 4,983,581 | A |   | 1/1991 | Antoniades et al. .......... 514/12 |
| 5,108,399 | A |   | 4/1992 | Eitenmuller et al. .......... 606/77 |
| 5,258,034 | A |   | 11/1993 | Furlong et al. ............... 623/23 |
| 5,281,419 | A |   | 1/1994 | Tuan et al. ................. 424/426 |
| 5,344,654 | A |   | 9/1994 | Rueger et al. .............. 424/423 |
| 5,397,572 | A |   | 3/1995 | Coombes et al. ........... 424/426 |
| 5,458,653 | A |   | 10/1995 | Davidson ..................... 623/23 |
| 5,466,609 | A |   | 11/1995 | Siiman et al. .............. 436/518 |
| 5,492,697 | A |   | 2/1996 | Boyan et al. ............... 424/422 |
| 5,502,074 | A |   | 3/1996 | Cullinan et al. ............ 514/443 |

(Continued)

FOREIGN PATENT DOCUMENTS

DE    39 33 217 A1    4/1991

(Continued)

OTHER PUBLICATIONS

Merriam Webster's Collegiate Dictionary, 10th Edition, Copyright 1999, p. 20.*

(Continued)

*Primary Examiner*—James M. Spear
*Assistant Examiner*—Humera N. Sheikh
(74) *Attorney, Agent, or Firm*—Jones Day (57) ABSTRACT

This invention relates to an implant for treating pathological changes in the spinal column and/or locomotor system. According to one embodiment of the invention, the implant may be provided with an enamel-like or varnish-like coating up to 100 μm thick and made of a biodegradable polymer such as polylactide. This coating has an osteoinductive effect, which promotes the healing of fractures. Additional osteoinductive materials such as growth factors may be incorporated in the coating. The invention also relates to a method for producing such an implant using the following steps: preparing a dispersion of biodegradable polymers in an organic solvent; applying the dispersion on the surface to be coated; and allowing the solvent to evaporate.

34 Claims, 8 Drawing Sheets

U.S. PATENT DOCUMENTS

| | | | |
|---|---|---|---|
| 5,514,380 A | 5/1996 | Song et al. | 424/426 |
| 5,548,035 A | 8/1996 | Kim et al. | 525/408 |
| 5,556,645 A | 9/1996 | Bockman et al. | 424/650 |
| 5,573,401 A | 11/1996 | Davidson et al. | 433/201.1 |
| 5,603,715 A | 2/1997 | Kessler | 606/63 |
| 5,614,496 A | 3/1997 | Dunstan et al. | 514/12 |
| 5,635,571 A | 6/1997 | Frechet et al. | 525/410 |
| 5,645,592 A | 7/1997 | Nicolais et al. | 623/16 |
| 5,656,598 A | 8/1997 | Dunstan et al. | 514/12 |
| 5,670,161 A * | 9/1997 | Healy et al. | |
| 5,686,116 A | 11/1997 | Bockman et al. | 424/650 |
| 5,697,976 A | 12/1997 | Chesterfield et al. | 623/11 |
| 5,707,877 A | 1/1998 | Siiman et al. | 436/518 |
| 5,725,491 A | 3/1998 | Tipton et al. | 602/43 |
| 5,756,145 A | 5/1998 | Darouiche | 427/2.24 |
| 5,759,564 A | 6/1998 | Milder et al. | 424/426 |
| 5,770,255 A | 6/1998 | Burrell et al. | 427/2.1 |
| 5,824,088 A | 10/1998 | Kirsch | 623/16 |
| 5,830,493 A | 11/1998 | Yokota et al. | 424/426 |
| 5,854,207 A | 12/1998 | Lee et al. | 514/2 |
| 5,876,446 A | 3/1999 | Agrawal et al. | 623/11 |
| 5,876,452 A | 3/1999 | Athanasiou et al. | 623/16 |
| 5,906,600 A | 5/1999 | Bähr | 604/265 |
| 5,916,585 A | 6/1999 | Cook et al. | 424/426 |
| 5,916,870 A | 6/1999 | Lee et al. | 514/2 |
| 6,086,908 A | 7/2000 | Göpferich | 424/424 |
| 6,530,951 B1 * | 3/2003 | Bates et al. | |

FOREIGN PATENT DOCUMENTS

| | | |
|---|---|---|
| DE | 41 30 545 A1 | 3/1993 |
| DE | 41 30 546 A1 | 3/1993 |
| DE | 43 34 272 C2 | 4/1995 |
| DE | 195 11 243 A1 | 1/1996 |
| DE | 195 14 104 C2 | 11/1996 |
| EP | 0 198 213 A2 | 10/1986 |
| EP | 0 366 018 | 5/1990 |
| EP | 0 198 213 B1 | 8/1990 |
| EP | 0 567 391 A1 | 10/1993 |
| EP | 0 636 377 A1 | 2/1995 |
| EP | 0 652 017 A1 | 5/1995 |
| EP | 0 395 187 B1 | 1/1996 |
| EP | 0 719 562 A1 | 7/1996 |
| EP | 0 792 654 A2 | 9/1997 |
| EP | 0 816 413 A2 | 1/1998 |
| EP | 0 850 651 A2 | 7/1998 |
| EP | 0 652 017 B1 | 8/1999 |
| WO | WO 88/10123 | 12/1988 |
| WO | WO 89/04674 | 6/1989 |
| WO | WO 90/13302 | 11/1990 |
| WO | WO 91/11148 | 8/1991 |
| WO | WO 92/00110 | 1/1992 |
| WO | 93/20859 | * 10/1993 |
| WO | WO 93/20859 | 10/1993 |
| WO | WO 94/03159 | 2/1994 |
| WO | WO 94/08635 | 4/1994 |
| WO | WO 95/22318 | 8/1995 |
| WO | WO 95/24211 | 9/1995 |
| WO | WO 95/34251 | 12/1995 |
| WO | WO 96/00592 | 1/1996 |
| WO | WO 96/05825 | 2/1996 |
| WO | WO 96/11403 | 4/1996 |
| WO | WO 96/18591 | 6/1996 |
| WO | WO 96/28196 | 9/1996 |
| WO | WO 96/38167 | 12/1996 |
| WO | WO 97/10849 | 3/1997 |
| WO | WO 97/24369 | 7/1997 |
| WO | WO 97/32594 | 9/1997 |
| WO | WO 97/34953 | 9/1997 |
| WO | WO 97/37848 | 10/1997 |
| WO | WO 97/38741 | 10/1997 |
| WO | WO 97/47254 | 12/1997 |
| WO | WO 98/03695 | 1/1998 |
| WO | WO 98/16268 | 4/1998 |
| WO | WO 98/19699 | 5/1998 |

OTHER PUBLICATIONS

R. Herrmann et al., "Antithrombogenic Coating of Stents Using A Biodegradeable Drug Delivery Technology," *Thromb Haemost*, 82: 51-57 (1999).

S. Trippel, et al., "Growth Factors As Therapeutic Agents," *The Journal of Bone and Joint Surgery*, 78-A(8):1272-1285 (Aug., 1996).

K. Nakamura et al., "Local Application of Basic Fibroblast Growth Factor Into the Bone Increases Bone Mass at the Applied Site in Rabbits," *Arch Orthop Trauma surg*, 115: 344-346 (1996).

T. Einhorn, "Current Concepts Review Enhancementv of Fracture-Healing," *The Journal of Bone and Joint Surgery, Incorporated*, 77-A(6):940-956 (Jun., 1995).

Nielsen et al., "Location injection of TGF-β Increases the Strength of Tibial Fractures in the Rat," *Acta Orthop Scand*, 65(1):37-41 (1994).

M. Lind et al., "Chemotaxis of Human Osteoblasts, Effects of Osteotropic Growth Factors," *APMIS*, 103:140-146 (1993).

M. Lind et al., "Transforming Growth Factor-β Enhances Fracture Healing in Rabbit Tibiae," *Acta Orthop Scand*, 64(5):553-556 (1993).

J. Andrew et al., "Demonstration of TGF-β1 mRNA by In Situ Hybridization in Normal Human Fracture Healing," *Calcif Tissue Int*, 52:74-78 (1993).

P. Wilton, "Treatment With Recombinant Human Insulin-Like Growth Factor I of Children With Growth Hormone receptor Deficiency (Laron Syndrome)," *Acta Paediatr Suppl*, 383:137-141 (1992).

J. Carpenter et al., "Failure of Growth Hormone to Alter the Biomechanics of Fracture-Healing in a Rabbit Model," *The Journal of Bone and Joint Surgery, Incorporated*, 74-A(3): 359-367 (Mar. 1992).

J. Hock et al., "Transforming Growth Factor-β Stimulates Bone Matrix Apposition and Bone Cell Replication in Cultured Fetal Rat Calvariae," *Endocrinology*, 126(1)421-426 (1990).

J. Hock et al., "Transforming Growth Factor-β Stimulates Bone Matrix Apposition and Bone Cell Replication in Cultured Fetal Rat Calvariae," *Endocrinology*, 126(1)421-426 (1990).

M. Noda et al., "In vivo Stimulation of Bone Formation by Transforming Growth Factor-β," *Endocrinology*, 124(6): 2991-2994 (1989).

J. Hock et al., "Insulin-Like Growth Factor I Has Independent Effects on Bone Matrix Formation and Cell Replication," *Endocrinology*, 122::254-260 (1988).

A. Nilsson et al., "Effects of Unilateral Arterial Infusion of GH and IGF-I on Tibial Longitudinal Bone Growth in Hypophysectomized Rats," *Calcif Tissue Int*, 40:91-96 (1987).

J. Isgaard et al., "Effects of Local Administration of GH and IGF-1 on Longitudinal Bone Growth in Rats," *The American Physiological Society*, pps. E367-E372 (1986).

H. Bail et al., "Histomorphometrical Evidence for the Bone Anabolic Effect of Species Specific Growth Hormone in Distraction Osteogenesis (DO)," *Intl. Soc. Fracture Repair*, Mar. 1998.

H. Bail et al., "Rekombinantes Wachstumshormon beschieunigt die Kallusreifung bei der Distraktionsosteogenese", 1998. (English translation of Abstract only).

R. Herrmann et al., "Comparison of the Thrombogenicity of Steel and Gold-Surface Coronary Stents with a Biodegradable, Drug Releasing Coating in a Human Stasis Model," Circulation 96:4048, 1997.

R. Hermann et al., "Comparison of the Thrombogenicity of Steel and Gold-Surface Coronary Stents with a Biodegradable, Drug Releasing Coating in a Human Stasis Model," European Heart Journal 18(152):988, 1997.

G. Schmidmaier et al., "Non-Linear Time Release Characteristics of a Biodegradable Polyactic Acid Stent Coating Releasing PEG-Hirudin and a PG12 Analog," European Heart Journal 18(571):3316, 1997.

G. Schmidmaier et al., "Neue Polylactid-Beschichtung für Koronarstents, die PEG-Hirudin und ein Prostacyclinanalog freisetzi, um die Aktivierung von Thrombozyten und der plasmatischen Gerinnung zu hemmen," Z Kardiol:86(51): 304, 1997. (In German, no translation available).

G. Schmidmaier et al., "Time Release Characteristics of a Biodegradable Stent Coating with Polylactic Acid Releasing PEG-Hirudin and PG12-Analog," J Am Coll Cardiol 29 (94A):927-3, 1997.

G. Schmidmaier et al., "A New Biodegradable Polylactic Acid Coronary Stent-Coating, Releasing PEG-Hirudin and a Prostacycline Analog, Reduces Both Platelet Activation and Plasmatic Coagulation," J Am Coll Cardiol 29(354A):771-5, 1997.

H. Bail et al., "Species Specific Growth Hormone Accelerates Bone Regenerate Healing in Distraction Osteogenesis," Proceedings from 2nd Consensus Meeting, European Tissue Repair Society, 1997.

H. Bail et al., "Recombinant Growth Hormone Increases Hard Callus Formation in Distraction Osteogenesis," 1997.

L. Beck et al., "TGF-$\beta_1$ Induces Bone Closure of Skull Defects: Temporal Dynamics of Bone Formation in Defects Exposed to rhTGF-$\beta_1$," Journal of Bone and Mineral Research 8(6):753-761, 1993.

S. Thaller et al., "The Effect of Insulin Growth Factor-1 on Calvarial Sutures in a Sprague-Dawley Rat," The Journal of Craniofacial Surgery 4(1):35-39, Jan., 1993.

J. Pfeilschifter et al., "Stimulation of Bone Matrix Apposition in Vitro by Local Growth Factors: A Comparison Between Insulin-like Growth Factor I, Platelet-Derived Growth Factor, and Transforming Growth Factor $\beta$, " Endocrinology 127(1):69-75, 1990.

F. Kandziora et al., "Experimentelle Spondylodese der Schafshalswirbels äule," Der Chrurg, 2002, 73:1025-1038.

M. Lucke et al., "Gentamicin coating of metallic implants reduces implant-related osteomyelitis in rats," Bone, 32 (2003), pp 521-531.

H. Bail et al., "Systemic application of growth hormone enhances the early healing phase of osteochondral defects-a preliminary study in micropigs," Bone, 32(2003), pp 457-467.

G. Schmidmaier et al., "Bone Morphogenetic Protein-2 Coating of Titanium Implants Increases Biomechanical Strength and Accelerates Bone Remodeling in Fracture Treatment: A Biomechanical and Histological Study in Rats," Bone, vol. 30, No. 6, Jun. 2002:816-822.

B. Wildemann et al., "Cell Proliferation and Differentiation During Fracture Healing Are Influenced by Locally Applied IGF-1 and TGF-$\beta$1: Comparison of Two Proliferation Markers, PCNA and BrdU," 2003 Wiley Periodicals, Inc., pp 150-156.

T. Pufe et al., "Quantitative measurement of the splice variants 120 and 164 of the angiogenic peptide vascular endothelial growth factor iin the time flow of fracture healing: a study in the rat," Cell Tissue Res, (2002) 309: 387-392.

F. Kandziora et al., "IGF-I and TGF-$\beta$1 Application by a Poly-(D,L-Lactide)-Coated Cage Promotes Intervertebral Bone Matrix Formation in the Sheep Cervical Spine," SPINE, vol. 27, Numer 16, pp 1710-1723, 2002.

F. Kandziora et al., "Bone morphogenetic protein-2 application by a poly(D,L-lactide)-coated interbody cage: in vivo results of a new carrier for growth factors," J Neurosurg (Spine), 97:40-48, 2002.

G. Schmidmaier et al., "Improvement of Fracture Healing by Systemic Administration of Growth Hormone and Local Application of Insulin-like Growth Factor-1 and Transforming Growth Factor-$\beta$1," Bone, vol. 31, No. 1, Jul. 2002:165-172.

G.Schmidmaier et al., "IGF-1 and TGF-Beta 1 Incorporated in a Poly(D,L-Lactide) Implant Coating Stimulates Osteoblast Differentiation and Collagen-1 Production but Reduces Osteoblast Proliferation in Cell Culture," 2003 Wiley Periodicals, Inc., pp 157-162.

M. Raschke et al., "Insulin-like Growth Factor-1 and Transforming Growth Factor-$\beta$1 Accelerates Osteotomy Healing Using Polyactide-coated Implants as a Delivery System: A Biomechanical and Histological Study in Minipigs," Bone, vol. 30, No. 1, Jan. 2002: 144-151.

M. Raschke et al., "Homologous Growth Hormones Accelerates Healing of Segmental Bone Defects," Bone, vol 29, No. 4, Oct. 2001:368-373.

G. Schmidmaier et al., "A New Electrochemically Graded Hydroxyapatite Coating for Osteosynthetic Implants Promotes Implant Osteointegration in a Rat Model," 2002 John Wiley & Sons, Inc., pp 168-172.

F. Kandziora et al., "Comparison of BMP-2 and combined IGF-1/TGF-$\beta$1 application in a sheep cervical spine fusion model," Eur Spine J, (2002), 11:482-493.

G. Schmidmaier et al., "Local Application of Growth Factors (Insulin-Like Growth Factor-1 and Transforming Growth Factor-$\beta$1) From a Biodegradable Poly(D,L-lactide) Coating of Osteosynthetic Implants Accelerates Fracture Healing in Rats," Bone, vol. 28, No. 4, Apr. 2001:341-350.

G. Schmiddmaier et al., "Biodegradable Poly(D,L-Lactide) Coating of Implants for Continuous Release of Growth Factors," 2001 John Wiley & Sons, Inc., pp 449-455.

* cited by examiner

Fig. 3 uncoated       PDLLA       PDLLA
                         + IGF-I + TGF-ß1

Fig. 7 uncoated  PDLLA  PDLLA + IGF-I + TGF-ß1

BIOLOGICALLY ACTIVE IMPLANTS

CROSS-REFERENCE TO RELATED APPLICATIONS

This application is a continuation of the U.S. National Stage designation of co-pending International Patent Application PCT/EP99/06708, filed Sep. 10, 1999, which claims priority to German Application No. 198 43 251.8, filed Sep. 11, 1998. The entire content of both of these applications is expressly incorporated herein by reference thereto.

FIELD OF THE INVENTION

The present invention relates to an implant designed to compensate for pathological changes or conditions in the spinal column and/or locomotor system. The invention also covers a method for producing such an implant.

BACKGROUND OF THE INVENTION

Implants for treatment of pathological conditions of the spine and/or locomotor system are known in the prior art. They are intended, for example, to mechanically stabilize a fracture, thus promoting the healing process or, in the case of endoprosthetic implants, to be permanently bonded to the bone.

PCT Publication No. WO 98/19699 describes the systemic administration of medications or hormones serving to promote osteosynthesis and thus to accelerate the healing process of the fracture. Examples of suitable means include growth factors such as IGF-I. Such systemic applications, however, can lead to undesirable side effects.

PCT Publication No. WO 93/20859 describes the fabrication of a thin foil or film consisting of a polylactic-acid/polyglycol-acid copolymer containing growth factors. The intent is to wrap a foil of that type, for instance, around fracture-fixation devices prior to their implantation. This is supposed to release the growth factors in localized fashion in the area of the fracture. In practice, however, this method is unsuitable since, for instance, a nail wrapped with a foil of that type cannot be inserted in the medulla in a way that the foil, which only loosely envelops the nail, actually reaches the point of its intended healing action.

In light of the foregoing, a need exists for an implant that promotes the healing process in pathological changes of the spinal column and locomotor system, especially by furthering osteosynthesis, and thus accelerating the healing of fractures or the integration of an implant.

SUMMARY OF THE INVENTION

The present invention relates to an implant for treating pathological changes or conditions in the spinal column and/or locomotor system. The implant, in various embodiments, has a varnish-like biodegradable polymer coating of a thickness of 100 $\mu$m or less, a thickness of 50 $\mu$m or less, preferably 30 $\mu$m or less, and more desirably, 20 $\mu$m or less. In other embodiments, the varnish-like coating has a thickness of 10 to 30 $\mu$m, and preferably 10 to 20 $\mu$m. The implant can be a fracture-fixation device or an endoprosthetic device. Examples of such devices include plates, screws, nails, pins, wires, threads, or cages used for the spinal column and locomotor system.

The polymer used for the coating may have a glass transition temperature of 37° C. (98.6° F.) or higher and a mean molecular weight of 100 kDa or less. Examples of suitable polymers include poly-$\alpha$ hydroxy acids, polyglycols, polytyrosine carbonates, starch, gelatins, and cellulose, as well as blends and interpolymers thereof. Examples of suitable poly-$\alpha$ hydroxy acids include polylactides, polyglycol acids, and interpolymers thereof.

The varnish-like coating according to the present invention can also include pharmaceutically active additives, such as osteoinductive substances. Examples of such substances include one or more growth factors. Specifically, the growth factors can be selected from the group consisting of IGF, TGF, FGF, EGF, BMP, and PDGF. In an exemplary embodiment, the coating contains IGF-I, TGF-$\beta$, or combinations thereof. In one embodiment, the growth-factor percentage of the total weight of the coating is 0.1 to 10% by weight, preferably 0.5 to 8% by weight and, more desirably, 1 to 5% by weight.

The present invention also relates to a method of producing an implant having a varnish-like biodegradable polymer coating of a thickness of 100 $\mu$m or less. Furthermore, the invention relates to an implant produced by such a method. The method for producing an implant includes the following steps: preparing a dispersion of the biodegradable polymer in an organic solvent; applying the dispersion on the surface to be coated; and allowing the solvent to evaporate. The application and evaporation processes may occur, for example, at a temperature of between 0 and 30° C. (32–86° F.), and preferably at about 22° C. (72° F.). Additionally, the evaporation of the solvent may occur, for example, in a gaseous atmosphere substantially saturated with solvent vapor. In an exemplary embodiment, the application of the dispersion and the evaporation of the solvent are repeated two or more times.

The dispersion may be a colloidal solution of the polymer in the solvent. Such a colloidal solution may be produced by allowing a mixture of polymer and solvent to stand for periods of time ranging from 1 minute to 24 hours, preferably 2 to 24 hours, 3 to 12 hours, or 4 to 8 hours, and most preferably for about 6 hours. The colloidal solution may be filtered prior to its application. The filtering may occur through a micropore filter with a pore size of 0.45 $\mu$m or smaller.

Suitable solvents include ethyl acetate or chloroform with the dispersion containing, for example, 20 to 300 mg of polymer per ml of solvent.

BRIEF DESCRIPTION OF THE DRAWINGS

Preferred features of the present invention are disclosed in the accompanying drawings, wherein similar reference characters denote similar elements throughout the several views, and wherein.

DETAILED DESCRIPTION OF PREFERRED EMBODIMENTS

The present invention relates to an implant having a varnish-like coating of a biodegradable or resorbable polymer that may be up to 100 μm thick. As used herein, the term implant refers to a device, which in the process of a surgical procedure is at least partially introduced inside the body. In an exemplary embodiment, the present invention is directed to implants of the type that serve to support a pathologically changed spinal column and/or locomotor system, especially by providing a mechanical reinforcement. The pathological changes may be in the form of fractures, pathological changes of joints and bones, distended or torn ligaments or tendons and the like. Application of the implants may involve direct contact with, attachment to or insertion in a bone of other part or element of the spinal column or locomotor system (such as ligaments or tendons).

The term implant is to be understood in the broadest sense of the word since it also includes, for instance, implants which are used for elongative or reductive ostectomies, craniotomies, for ligament healing and restoration, for tumor and sports-injury-related surgery, in dentistry as well as in the case of oral, maxillary and facial dislocations.

The term fracture fixation device refers to any device that serves to fix, correct and/or mechanically stabilize a fractured bone. Examples thereof include plates, screws, nails, pins, wires, sutures, or cages for the spinal column and locomotor system. Usually, fracture fixation devices are removed after the fracture has healed, but in certain circumstances, they may be permanently left in or on the bone or they can be reabsorbed by the organism. Endoprosthetic implants are designed to permanently remain in the body and usually function as substitutes for a natural body part such as a joint, a bone section or a tooth.

The implants according to one embodiment of the invention are made of a base material that is chemically and/or physically different from that of the varnish-like coating. In many cases, the base material may not be biodegradable. This implies that under physiological conditions, where the implant is used and for the length of time during which it is typically retained in the body, the base material will not decay, corrode or in any other way change its physiochemical state, or if it does, then only with negligible deterioration of its desired effect. An implant according to one aspect of the invention will in many cases consist of a metal or an alloy such as stainless steel or titanium. Alternatively, the implant may consist of a base material which is itself biodegradable or bioresorbable.

In accordance with the present invention, the implants are provided with a varnish-like coating. The term varnish-like means that the coating bonds with the surface of the base material with enough adhesive strength such that, when the implant is implanted, mechanical friction will not abrade or otherwise damage the coating, or at least, not to such an extent as to compromise its physical effect, as described in more detail further below. For example, it is advantageous to properly drive a nail, provided with the varnish-like coating, into the bone without any significant abrasion of the varnish-like coating.

The coating may be up to 100 μm thick. In other words, it is preferable that the average thickness of the coating is 100 μm or less. For example, spots with a thickness of more than 100 μm, occasioned by fluctuations in the coating process, would be allowed.

The coating consists of a biodegradable polymer. This means that, due to its exposure to the physiological conditions prevailing in the area of the implant, it will progressively degrade, over a period of preferably several weeks, months, or years, through molecular breakdown. These molecular separation products and any other metabolites preferably display no or, at worst, only negligible toxicity and the body should be able to metabolize or excrete all or most of them. Polymers, which contain no toxic metabolites and can be completely biodegraded and eliminated, are also sometimes referred to as bioresorbable. The polymers used in applying this invention are preferably of the bioresorbable type.

It is surprising that, even without the addition of other pharmaceutically active agents such as growth factors, the varnish-like coating promotes osteosynthesis (and thus contributory fracture-healing, infection-fighting, and complication-avoiding effect).

The thickness of the varnish-like coating is preferably 50 μm, more preferably about 30 μm, and most preferably about 20 μm or less. In many cases, the preferred thickness is between 10 and 30 μm and most desirably between 10 and 20 μm.

The polymer employed preferably has a glass transition temperature of 37° C. (98.6° F.) or higher so as to retain its desired strength in the body. Polymers with a mean molecular weight of 100 kDa or less are preferred.

The polymer is preferably selected from the group comprising poly-α-hydroxy acids, polyglycols, polytyrosine carbonates, starch, gelatins, cellulose as well as blends and interpolymers containing these components. Particularly preferred among the poly-α-hydroxy acids are the polylactides, polyglycol acids, and their interpolymers. One example of a suitable polylactide is marketed by Boehringer-Ingelheim under the trade name R 203. It is a racemic poly-D,L-lactide. This racemic compound forms an amorphous, varnish-like layer on the surface of the implant. The formation of crystalline polymer structures in the coating should preferably be avoided, which is why an enantiomerically pure lactide is preferably avoided. Suitable polytyrosene carbonates include for instance p(DTE-co-5% PEG 1000 carbonates) and p(DTE-co-26% PEG 20000 carbonates). These are copolymers containing the specified amounts of polyethylene glycols.

The coating may contain additional pharmaceutically active agents, such as osteoinductive or biocidal or anti-infection substances. Suitable osteoinductive substances include, for example, growth factors whose proportion of the total weight of the coating is preferably 0.1 to 10% by weight or, more preferably, 0.5 to 8% by weight and, most desirably, 1 to 5% by weight. This weight percentage relates to the net amount of the active agent, without counting any pharmaceutical carrier substances.

The growth factors may be selected from the group of IGF (insulin-like growth factors), TGF (transforming growth factors), FGB (fibroblast growth factors), EGF (epidermal growth factors), BMP (bone morphogenic proteins) and PDGF (platelet-derived growth factors). These growth factors are well known and are commercially available. The varnish-like coating preferably contains the IGF-I or TGF-β growth factors, with particular preference given to a combination of these two growth factors.

This invention also relates to a method for producing an implant of the type described above, which may include the steps of:

Preparing a dispersion of the biodegradable polymer in an organic solvent;

Applying the dispersion on the surface to be coated; and

Allowing the solvent to evaporate.

The term dispersion refers to any given distribution of the polymer in an organic solvent. This may be a chemical solution, a purely physical dispersion or any intermediate step, especially including for instance, colloidal solutions. The application of the dispersion and the evaporation of the solvent preferably take place at a temperature of between 0 and 30° C. (32–86° F.), and more desirably at a room temperature of about 22° C. (72° F.). This so-called cold coating also allows for temperature-sensitive components such as certain growth factors to be applied on the implant together with the polymer. Applying the dispersion is performed preferably by immersing the implant in the dispersion. Other ways of applying the coating, for example by brushing, spraying, etc. are also possible. Of course, in addition to the polymer, the dispersion may also contain the aforementioned pharmaceutically active agents such as osteoinductive or biocidal substances.

Most preferably, the solvent is allowed to evaporate in a gas atmosphere, essentially saturated with solvent vapor. To that end, it is desirable to manipulate the implant that has been immersed in the dispersion, in a closed space whose atmosphere is highly solvent-saturated. Preferably, this will result in a very slow evaporation of the solvent, and consequently, in a uniform, well-adhering varnish-like coating. The preferred evaporation time is between 1 minute and 1 hour, or more preferably 5 to 30 minutes, and most desirably about 10 minutes. It is also preferred to apply the coating by incrementally building it up in several thin layers, for example by repeating the dispersion and the solvent-evaporation processes two or more times.

Preferably, a dispersion which is constituted by a colloidal solution of the polymer in the solvent may be used. This colloidal solution preferably contains colloidal polymer particles between 1 and 1000 nm and preferably less than 400–500 nm in size. For example, this type of colloidal solution can be produced by mixing the polymer and the solvent, then letting it stand for a period of 1 minute to 24 hours, preferably 2 to 24 hours, more preferably 3 to 12 hours, still more preferably 8 hours, and most desirably about 6 hours. During the most preferred period of about 6 hours, polymer colloid particles will form in the desired size range of less than about 500 nm. To separate any remaining larger polymer particles, the colloidal solution can be filtered prior to its application on the implant, preferably by using a micropore filter whose pore size corresponds to the desired maximum size of the colloid particles. Micropore filters are commercially available with pore sizes for example of 0.45 or 0.2 $\mu$m.

The solvents used are preferably popular organic, nonpolar or weakly polar solvents. Particular preference may be given to ethyl acetate or chloroform. Prior to its application on the implant, the dispersion preferably contains an amount of, preferably 20 to 300 mg, and more desirably 50 to 150 mg, polymer (perhaps including other constituents such as osteoinductive or biocidal substances) per ml of solvent.

These and other aspects of the present invention may be more fully understood with reference to the following non-limiting examples, which are merely illustrative of the preferred embodiments of the present invention, and are not to be construed as limiting the invention, the scope of which is defined by the appended claims.

EXAMPLE 1

Method for Making a Bioactive Implant 400 mg PDLLA (poly(D,L) lactide, Resomer R 203 by Boehringer-Ingelheim) is dispersed in 6 ml chloroform at room temperature. If the coating is to contain other osteoinductive or biocidal substances, these are also added to the dispersion, in which case 400 mg is the total combined weight of the PDLLA and the additives. The dispersion is allowed to sit for 6 hours until a colloidal solution has formed, which is then passed through a sterile microfilter with a pore size of 0.45 $\mu$m into a sterile container.

Next, Kirschner wires (1.6 mm in diameter, 3.5 cm long) of titanium and steel as well as titanium bone nails are immersed in the filtered solution, whereupon the solvent is allowed to evaporate in a chloroform atmosphere for a period of 10 minutes. This process (coating and evaporation) is repeated once. The implants obtained preferably will be coated with a thin, varnish-like polymer layer about 10 to 20 $\mu$m thick.

EXAMPLE 2

Microbiological Properties of the Coating

After an incubation time of either 6 or 12 weeks, microbiological examinations of titanium Kirschner wires coated with a layer of PDLLA according to example 1 revealed no noticeable growth of microorganisms. Additionally, ten implants coated with PDLLA and ten uncoated implants were each contaminated with staphylococci (KD $10^5$). The coated implants displayed a significantly lower adhesion rate of these microorganisms.

EXAMPLE 3

Mechanical Strength of the Coating

Twenty titanium and steel Kirschner wires each were weighed and then coated, as in Example 1, with PDLLA containing 1% methyl violet as color marker. The wires were implanted in the tibiae of rats. Following explantation, the mechanical abrasion of the coating was measured by weighing and by photometric analysis. The highest abrasion rate found was 2.9% in the case of titanium wires and 4.6% for steel wires. Raster electron micrographs showed that in none of the implants examined had the coating been abraded all the way to the metal surface.

EXAMPLE 4

Method for Making a Bioactive Implant

This example will show the advantages of a colloidal solution for the mechanical strength of the coating. 800 mg each of PDLLA R 203 was added to 2 batches of 6 ml ethyl acetate each. The resulting dispersions were allowed to sit at room temperature for either 6 or 24 hours respectively and were then filtered as in Example 1. The dispersions or solutions thus obtained were used to coat stents, employing the procedure per Example 1. It should be mentioned that although stents are not orthopaedic implants, they were used only because they are particularly well suited for elongation tests, and, as a result, for the analysis of the mechanical strength of the varnish-like coating. The volume of the coating was determined by weighing the stents before and after the application of the coating. The coated stents were expanded with a PTCA balloon at a pressure of 8 bar (116 psi) using conventional techniques. The expanded stents were weighed again to determine the amount of the coating material that had peeled off or was lost some other way.

It was found that the stents which were coated with the dispersion that had stood for 6 hours prior to the filtering had lost an average of 0.8% of their coating while the other stents (which had stood for 24 hours) had a loss of 6.0% by weight. This indicates that for mechanical strength of the coating, it is preferable not to produce a complete chemical polymer solution in the solvent, but rather, a colloidal solution with a colloidal particle size of 0.45 μm or less.

EXAMPLE 5

Stability of the Active Agents Contained in the Coating

To determine the stability of the growth factors (WF) incorporated in the coating, titanium Kirschner wires were coated with PDLLA as in Example 1, containing the growth factors IGF-I (5% by weight) and TGF-βI (1% by weight). The stability (storage life) of the growth factors was analyzed after 6 weeks, 6 months and 1 year. After 6 weeks, the loss in effectiveness was found to be less than 3%. After 6 months, the growth factors included in the coating were found to be still better than 95.5% effective; and after 1 year better than 93%. This proves that the active agents, incorporated in the coating as provided for by the invention, retain their biological stability and effectiveness even if the coated implant is stored for an extended period of time before it is used.

EXAMPLE 6

Biodegradation of the PDLLA Coating

Titanium Kirschner wires, coated with PDLLA per Example 1, were subjected to in-vitro elutriation tests. To simulate in vivo situations, the elutions were passed through a physiological 0.9% NaCl solution at a temperature of 37° C. (98.6° F.) under laminar air-flow conditions. Within 9 weeks about 10% of the PDLLA coating had progressively degraded. For an in vivo study of the biodegradation characteristics of the PDLLA coating, 10 PDLLA-coated Kirschner wires with a defined coating volume were implanted in Sprague Dawley rats. After 6 weeks, the implants were removed and the in vivo degradation of the PDLLA coating was determined by measuring the difference between the pre-implantation and the post-explantation weight, as well as the inherent viscosity, and the molecular weight of the completely separated coating, followed by a comparison with the in vitro data.

Figure 1:
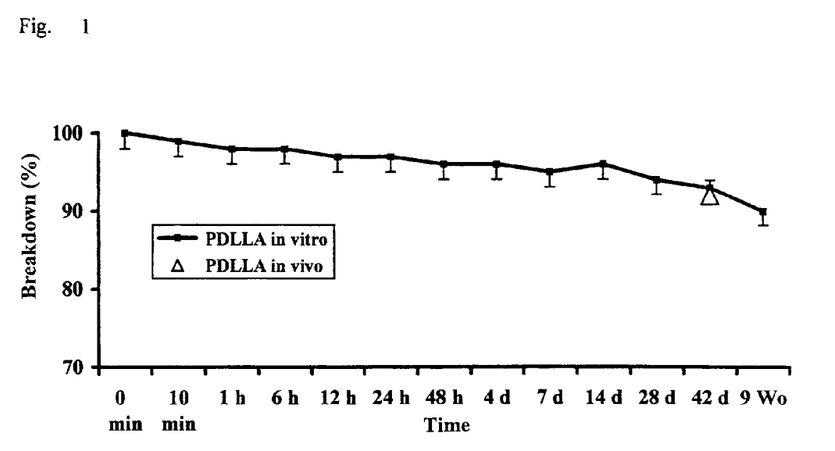
FIG. 1 shows the degradation of a polylactide coating on an implant according to the present invention as a function of time both in vivo and in vitro.

As shown in FIG. 1, about 10% of the PDLLA coating had biodegraded within 9 weeks. The comparative in vivo measurement shows that at that point in time, the in vitro and in vivo results were fairly identical.

EXAMPLE 7

Examination of the Release of Active Agents Integrated in the Coating

Figure 2:
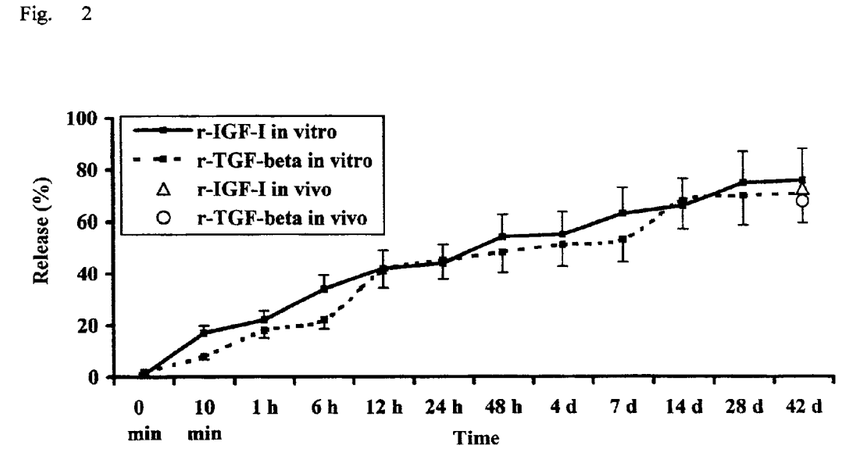
FIG. 2 shows the release of growth factors contained in the polylactide coating as a function of time.

As in Example 1, titanium Kirschner wires were coated with PDLLA, which additionally contained either 5% by weight of IGF-I or 1% by weight of TGF-β1 or a combination of 5% by weight of IGF-I and 1% by weight of TGF-β1. The release pattern of the growth factors incorporated in the coating was analyzed with in vitro elutriation tests. The results are shown in FIG. 2. Within 48 hours, an initial release of growth factors from the coating took place at a rate of 48 to 54%. From there, the release continued progressively until after 6 weeks, a total of between 71 and 78% of the growth-factor inclusions were released.

Ten titanium Kirschner wires, coated with PDLLA and the above-mentioned growth factors, were implanted in the tibiae of each of the Sprague Dawley rats used. After 42 days, the implants were removed and the residual concentrations of the growth factor inclusions were measured, using ELISA. As shown in FIG. 2, the in vivo results matched those of the in vitro elutriation tests.

EXAMPLE 8

Osteoinductive Effect of the Implants

In an experiment with animals, tests were conducted on 60 such animals (5-months-old female Sprague Dawley rats). All test animals were subjected to a standardized fracture of the right tibia. Differently coated titanium wires (1.0 mm in diameter) were then implanted in the repositioned tibiae as intramedullary supports.

Depending on the group assignments as specified below 2 mg/kg of a rat-specific recombinant growth hormone (r-rGH) or a placebo was subcutaneously injected daily for a period of time up to 42 days. At various time points (0 d, 4 d, 7 d, 14 d, 21 d, 28 d, 35 d, and 42 d) and after administration of an anaesthetic inhalant, x-rays were taken in two planes, 1.25 ml of blood was taken from each by the retrobulbar method (deep-frozen at −80° C. (−112° F.)), and their weight and body temperature were measured. On day 42, the fractured and the unfractured tibiae, along with the periosteum, were separately prepared and subjected to biomechanical tests (torsional load—torsional stiffness).

|  | Group assignments |
|---|---|
| Group I: | Fracture of the right tibia - uncoated implant - Systemic application of a placebo (control group) |
| Group II: | Fracture of the right tibia - implant coated with poly-D,L-lactide 203 - Systemic application of a placebo |
| Group III: | Fracture of the right tibia - implant coated with poly-D,L-lactide - Systemic application of (r-rGH) |

-continued

Group assignments

Group IV: Fracture of the right tibia - implant coated with poly-D,L-lactide and growth factors IGF-I (5%) and TGF-β (1%) - Systemic application of a placebo Group V: Fracture of the right tibia - implant coated with poly-D,L-lactide and growth factors IGF-I (5%) and TGF-β (1%) - Systemic application of (r-rGH)

The coated implants were produced as indicated in Example 1.

Results:

Fracturing

The fracturing model employed lent itself well to the creation of a standardized transverse fracture of the right tibia, without any major damage to the soft tissue. In 2 out of 60, the tibia fracture was comminuted; in one, it was helical, requiring premature discontinuation. One animal died in a postoperative examination under anesthesia (32nd day).

Weight and Temperature

In the animals systemically treated with (r-rGH) (Groups III and V), there was no rise in body temperature during the course of the test, in comparison to the animals that had been given a placebo (Groups I, II and IV), but their body weight increased significantly by 13% (p<0.05). No major differences were found among Groups I, II and IV (placebo) or III and V (GH).

Biomechanical Test

Figure 9:
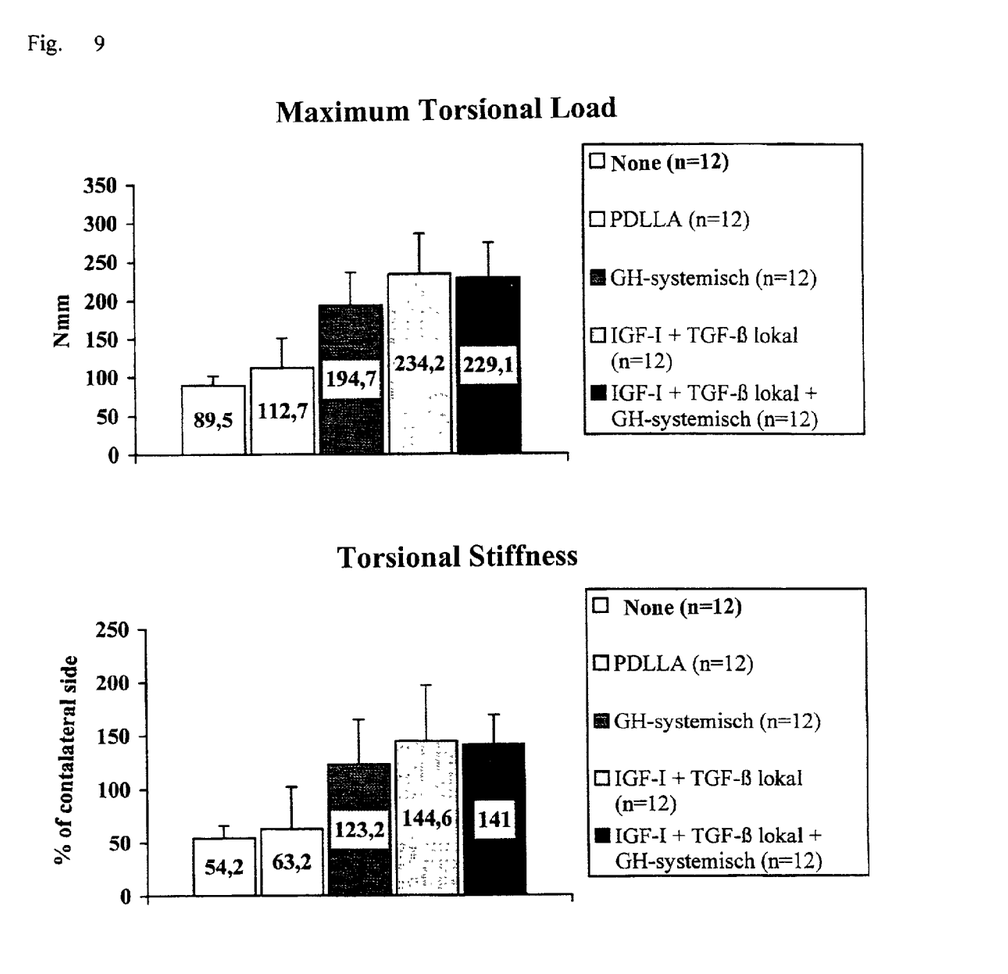
FIG. 9 shows the maximum torsional load and torsional stiffness in another examination of tibia fractures in rats.

The data obtained are expressed in absolute values (torsional load) and in percentages (torsional stiffness), as compared to the unfractured opposite side. The results reveal a significant increase (p<0.05) of the maximum torsional load in Group III, as well as Groups IV and V, as compared to the systemic application. It appears that the local application of growth factors (Group IV) not only leads to a markedly higher maximum torsional load, compared to the control group, but on average also when compared with the results of the systemic application of r-rGH (insignificant). No further increase in the maximum torsional load was observed as a result of simultaneous administration of r-rGH and the local application of IGF-I and TGF-β. The maximum torsional load in the group treated with poly-D,L-lactide increased significantly, compared to that of the control group. In terms of torsional stiffness, relative to that of the contralateral tibia, comparable findings were made. In this case as well, the groups with the local application of growth factors showed the most favorable results. FIG. 9 summarizes these results.

EXAMPLE 9

5 months-old female Sprague Dawley rats (n=144) were subjected to a standardized closed fracture of the right tibia using a fracturing machine; and uncoated versus coated titanium Kirschner wires were implanted in the tibiae as intramedullary stabilizers. A comparison was made between the following groups:

Group I: Uncoated implant (control group)
Group II: Implant coated with PDLLA ® 203)
Group III: Implant coated with PDLLA + r-IGF-I (5%)
Group IV: Implant coated with PDLLA + r-IGF-I (5%) + TGF-β1 (1%)

The coated implants were produced as in Example 1. Time-sequential radiographs were taken in 2 planes (a.-p. and lateral). At time points 0 d, 4 d, 7 d, 14 d, 21 d, 28 d, sera were measured, including the systemic concentration of r-IGF-I and r-TGF-β1 and the body weight and body temperature were determined. After 4 weeks, the implants were removed and the fractured tibiae were biomechanically tested in comparison with the untreated contralateral tibiae. The histomorphometric examination (O. Safranin/v.Kossa) of the calli was quantified by means of an analytical imaging system (Zeiss KS 400).

Figure 3:
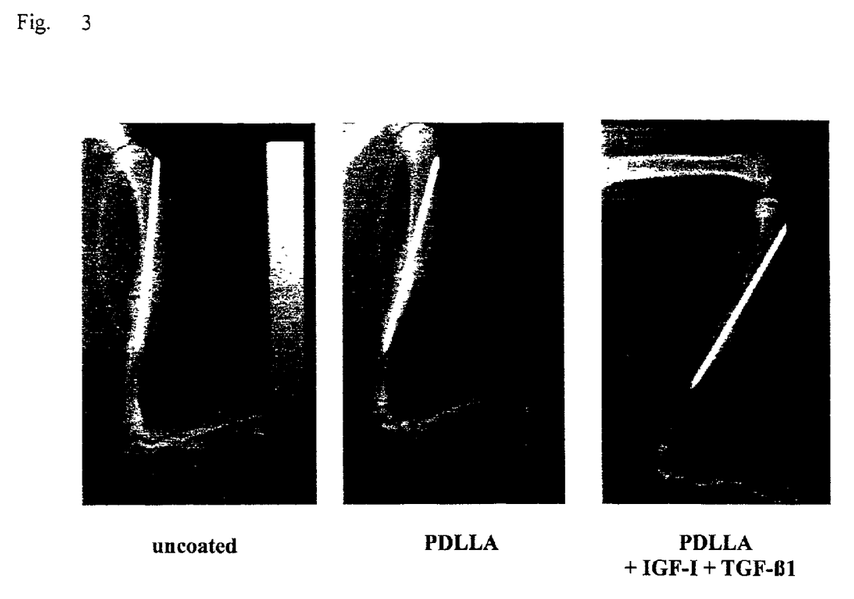
FIG. 3 shows a radiographic comparison of the effect of implants having a coating according to the present invention versus untreated (uncoated) implants on fracture healing in rats.
Figure 4:
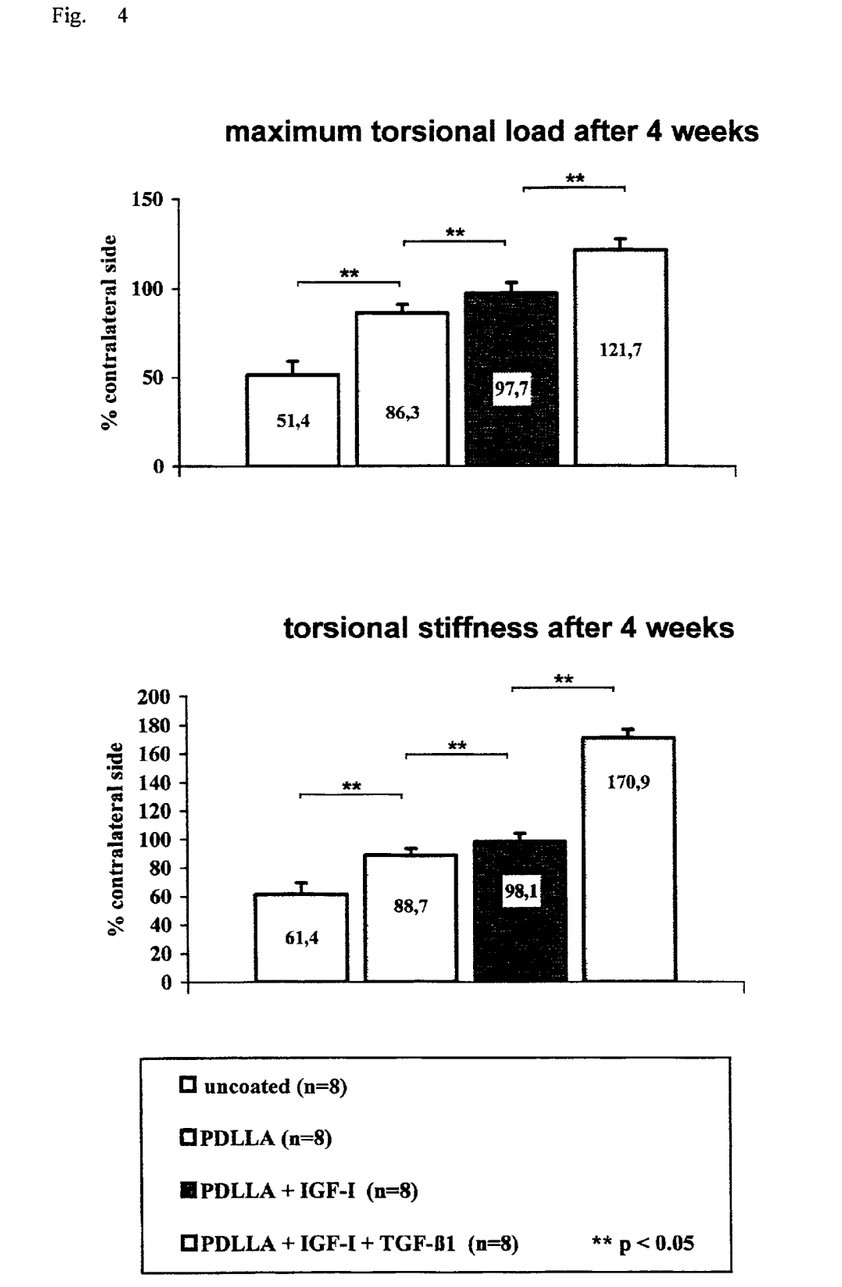
FIG. 4 shows a biomechanical comparison of the implants of FIG. 3.

In the radiographic evaluation, the untreated Group I still showed a distinct fractured dissociation. Groups II and III displayed good callus formation, as compared to the uncoated Group I. In the animals of Group IV, the fractures had almost completely consolidated (FIG. 3). Compared to the untreated contralateral tibia, and in a comparison with all other groups, the biomechanical tests revealed for Group IV a significantly higher maximum torsional load and maximum torsional stiffness. The combined application of r-IGF-I and r-TGF-β1 produced a substantially higher maximum torsional load and maximum torsional stiffness, compared to the group treated with IGF-I. The group treated with polylactide showed a significantly higher maximum torsional load and maximum torsional stiffness than the untreated Group I (FIG. 4).

Figure 5:
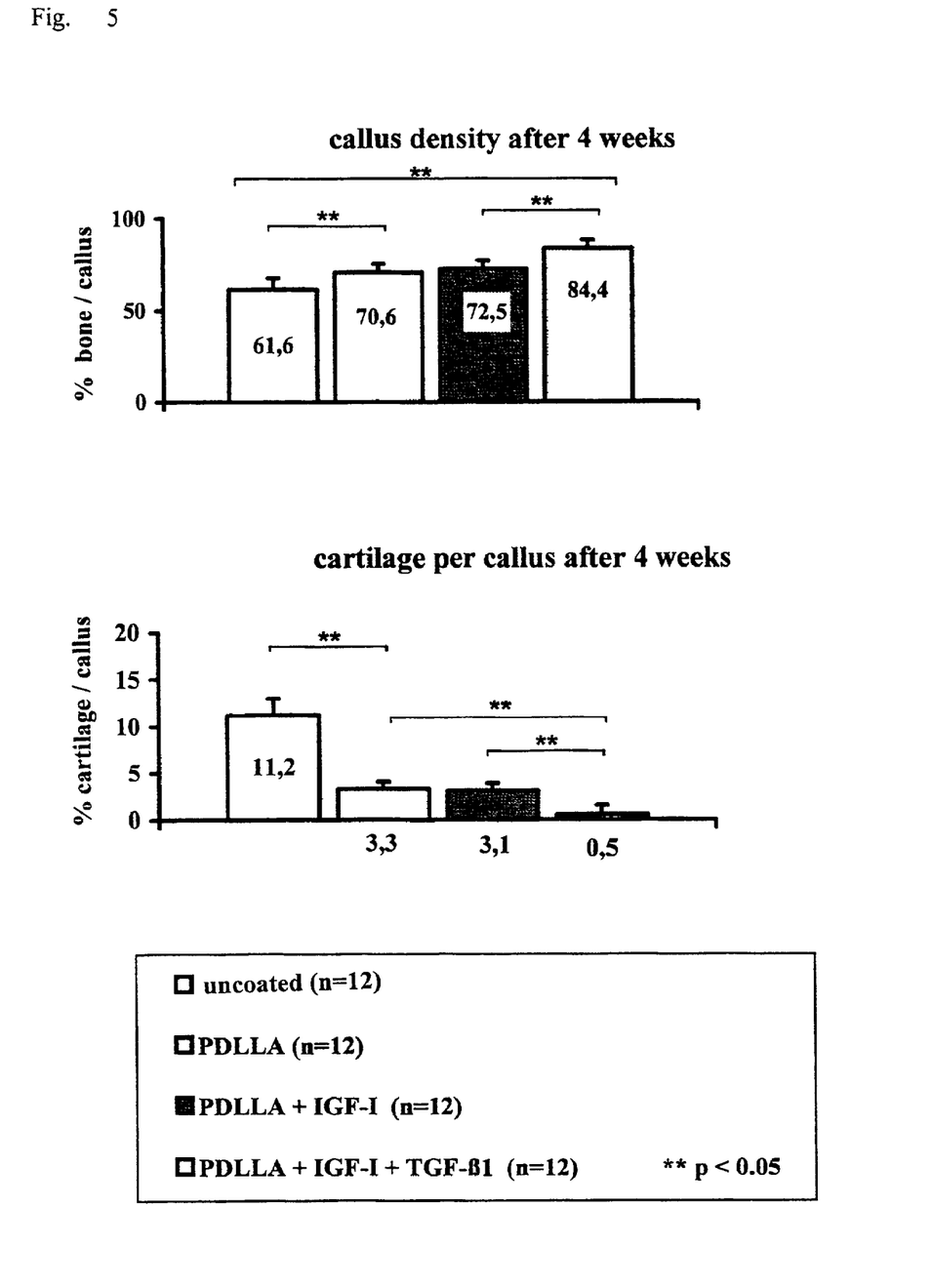
FIG. 5 shows a histomorphometric comparison of the implants of FIG. 3.
Figure 6:
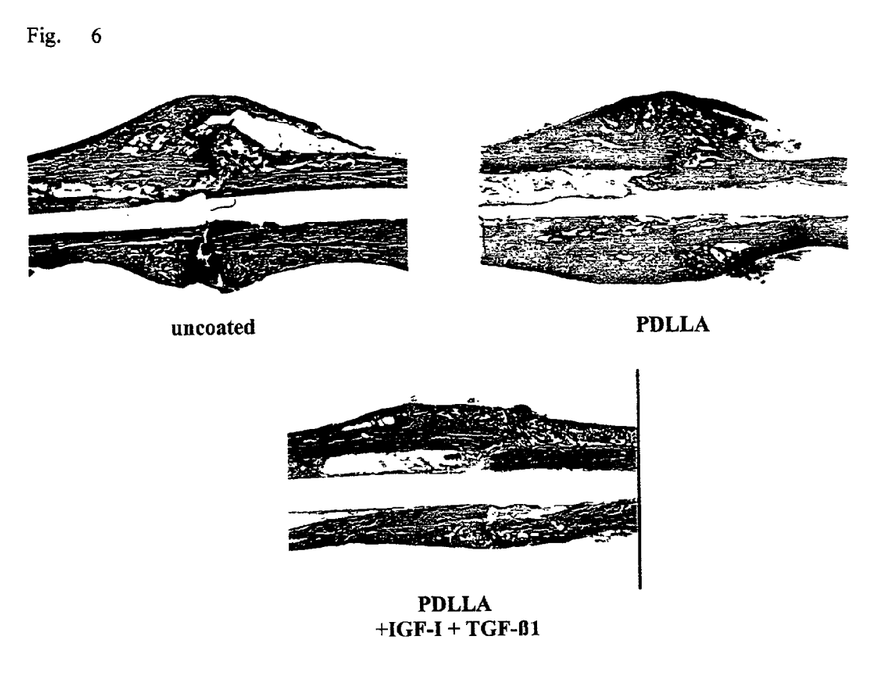
FIG. 6 shows illustrations of histomorphometric examinations.

The histomorphometric examinations substantiate the radiographic and biomechanical test results. There were substantially more areas of connective tissue cells in Group I than in the treated groups. The group treated with PDLLA displayed good callus formation and a pattern of advanced callus reconstruction, with a minimal proportion of connective tissue cells. Group IV displayed an almost completely restored fracture and the highest bone density in the callus. The group treated with polylactide only also showed a significantly higher bone density in the callus area, as compared with the control group (FIGS. 5 and 6).

Between the treated and the untreated groups, no changes were evident in terms of serum parameters, body weight, or body temperature.

EXAMPLE 10

12 months-old Yucatan dwarf pigs (n=30) were subjected to a standardized osteotomy (1 mm gap) of the right tibia which was then intramedullarily stabilized with either coated or uncoated titanium tibia nails and statically locked. A comparison of the following groups was made:

| | |
|---|---|
| Group I: | Uncoated implant (control group) |
| Group II: | Implant coated with PDLLA ® 203) |
| Group III: | Implant coated with PDLLA + r-IGF-I (5%) + TGF-β1 (1%) |

The coated implants were produced as in Example 1. Time-sequential radiographic examinations and serum tests were performed. After 4 weeks, the two tibiae were removed and biomechanically tested. The callus diameter was measured and the callus volume was determined by the Archimedes principle.

Results

Figure 7:
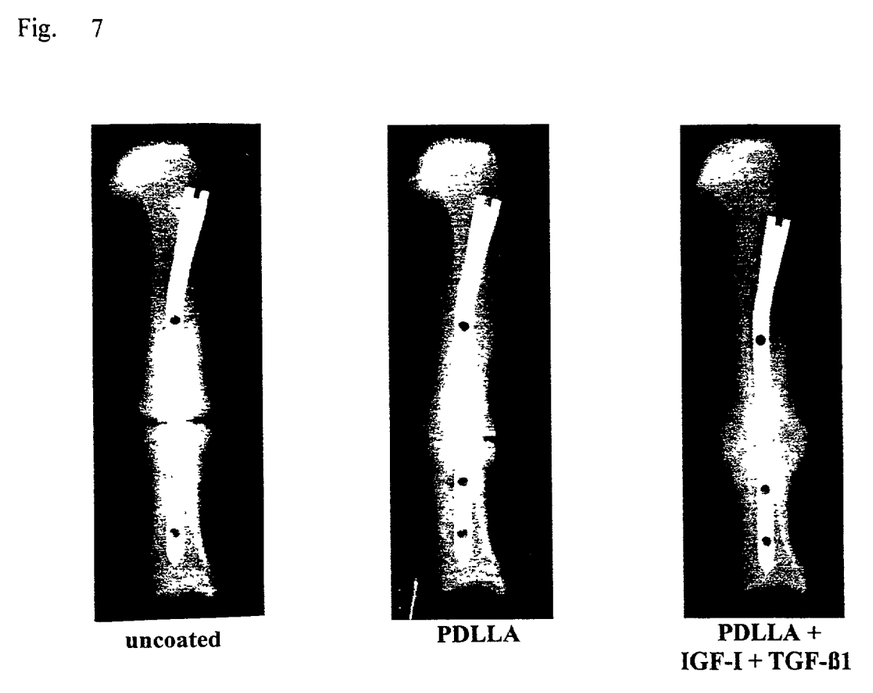
FIG. 7 shows a radiographic comparison between coated and uncoated implants in Yucatan pigs.
Figure 8:
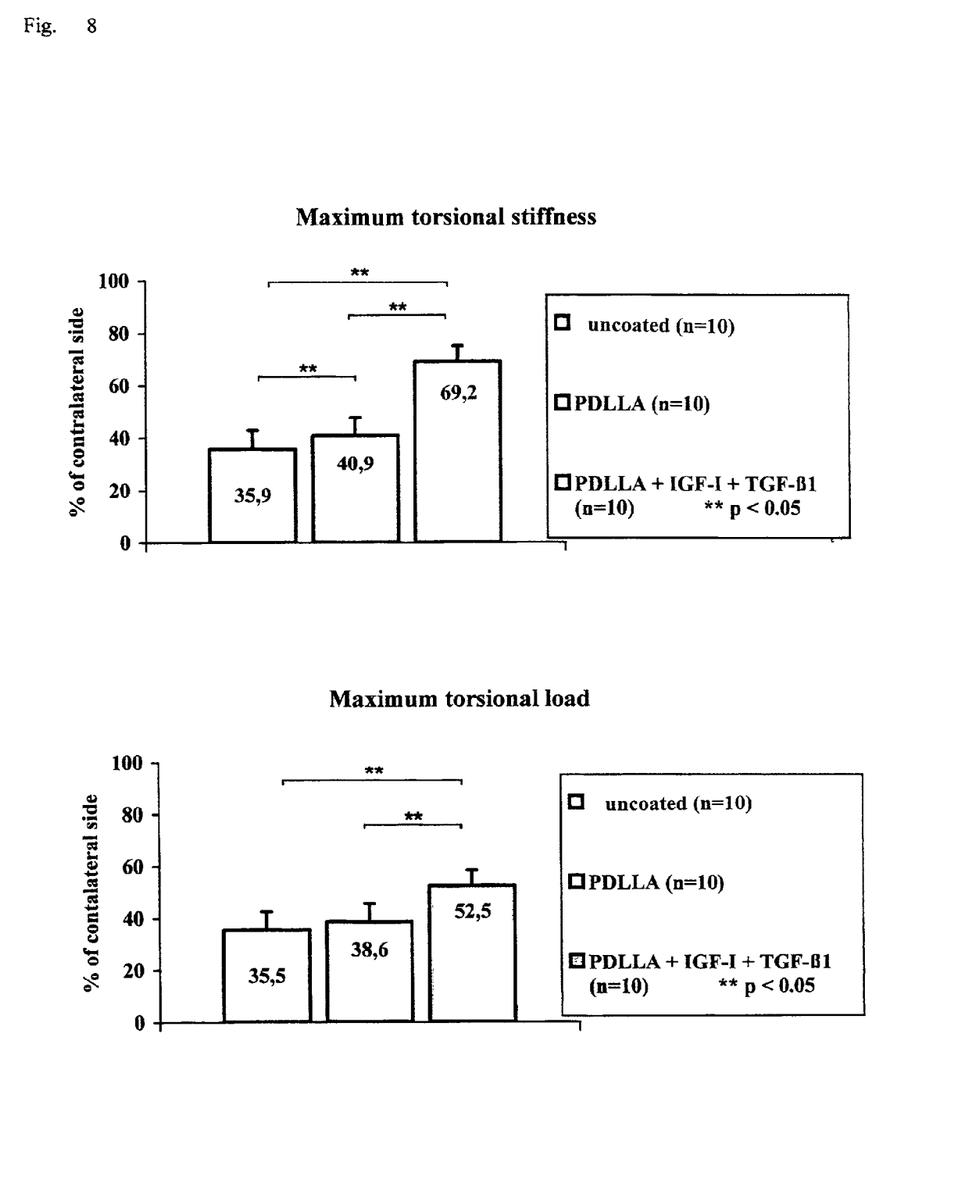
FIG. 8 is a biomechanical comparison of the implants of FIG. 7.

After 4 weeks, all of the control-group animals showed an incomplete consolidation of the osteotomy gap. The group treated with polylactide showed good callus formation. Group III displayed substantially advanced callus formation (FIG. 7). In Group II, treated with polylactide, and Group III, additionally treated with growth factors, the callus volume and callus diameter were significantly greater than in the control group.

Compared to the contralateral tibia, and in comparison with the control group, the group treated with polylactide displayed a considerably higher maximum torsional load and maximum torsional stiffness. The inclusion of growth factors in the polylactide coating produced a significant augmentation of the maximum torsional load and maximum torsional stiffness.

Strength of the Intramedullary Support

The standardized explantation of the titanium wires from the tibiae, using a power extractor, required substantially more extractive force for explanting the wires coated with IGF-I and TGF-β than those in the control group.

It is evident from Examples 8 to 10 that the use of an implant coated with a varnish-like biodegradable polymer coating can significantly accelerate the osteosynthesis and thus the healing process of the fracture. This accelerated process has been documented for a polymer-coated implant, without the addition of other osteoinductive agents. Incorporating growth factors in the coating permits a further acceleration of the fracture-healing process, with the combined application of IGF-I and TGF-β being particularly effective.

The examples also show that by means of the method per this invention, it is possible to produce a varnish-like coating, which by virtue of its physical structure and mechanical strength clearly distinguishes itself from any prior art.

While various descriptions of the present invention are described above, it should be understood that the various features can be used singly or in any combination thereof. Therefore, this invention is not to be limited to only the specifically preferred embodiments depicted herein.

Further, it should be understood that variations and modifications within the spirit and scope of the invention may occur to those skilled in the art to which the invention pertains. Accordingly, all expedient modifications readily attainable by one versed in the art from the disclosure set forth herein that are within the scope and spirit of the present invention are to be included as further embodiments of the present invention. The scope of the present invention is accordingly defined as set forth in the appended claims.

What is claimed is:

1. An implant for compensating for pathological changes in the spinal column or locomotor system, the implant comprising a surface and a body having a varnish-like coating of a thickness of 100 μm or less and made of a biodegradable polymer, wherein the body has a substantially constant physiochemical state under physiological conditions in vivo;

the varnish-like coating forms an adhesive bond to the surface of the implant; and the biodegradable polymer has a mean molecular weight of 100 kDa or less, and wherein said implant is made by:

a. preparing a dispersion of the biodegradable polymer in an organic solventl;

b. applying the dispersion on the surface of the implant; and c. evaporating the organic solvent.

2. The implant of claim 1, wherein the implant is a fracture-fixation or endoprosthetic device.

3. The implant of claim 2, wherein the fracture-fixation device is selected from the group consisting of a plate, screw, nail, pin, wire, thread, and cage.

4. The implant of claim 1, wherein the varnish-like coating has a thickness of 50 μm or less.

5. The implant of claim 4, wherein the varnish-like coating has a thickness of 10 to 30 μm.

6. The implant of claim 1, wherein the biodegradable polymer has a glass transition temperature of more than 37° C. (98.60° F.).

7. The implant of claim 1, wherein the biodegradable polymer is selected from the group consisting of poly-α hydroxy acids, polyglycols, polytyrosine carbonates, starch, gelatins, cellulose, and blends and interpolymers thereof.

8. The implant of claim 7, wherein the poly-α hydroxy acid biodegradable polymer is selected from the group consisting of polylactides, polyglycol acids, and interpolymers thereof.

9. The implant of claim 1, wherein the varnish-like coating contains a pharmaceutically active additive.

10. The implant of claim 9, wherein the pharmaceutically active additive includes an osteoinductive substance.

11. The implant of claim 10, wherein the osteoinductive substance contains a growth factor.

12. The implant of claim 11, wherein the growth factor is present in an amount from 0.1 to 10 by weight percentage of the coating.

13. The implant of claim 12, wherein the growth factor is present in an amount from 0.5 to 8 weight percentage of the coating.

14. The implant of claim 13, wherein the growth factor is present in an amount from 1 to 5 weight percentage of the coating.

15. The implant of claim 11, wherein the growth factor includes at least one of IGF, TGF, FGF, EGF, BMP, and PDGF.

16. The implant of claim 11, wherein the growth factor is IGF-I or TGF-β.

17. The implant of claim 11, wherein the growth factor is a mixture of IGF-I and TGF-β.

18. The implant of claim 17, wherein the coating contains about 5% by weight of IGF-I and 1% by weight of TGF-β.

19. The implant of claim 1, wherein the coating contains at least two layers of the biodegradable polymer.

20. A method for making an implant for compensating for pathological changes in the spinal column or locomotor system, the implant comprising a surface and a body having a varnish-like coating of a thickness of 100 μm or less and made of a biodegradable polymer, wherein the body has a substantially constant physiochemical state under physiological conditions in vivo;

the varnish-like coating forms an adhesive bond to the surface of the implant; and the biodegradable polymer has a mean molecular weight of 100 kDa or less, and the method comprising the steps of:

a. preparing a dispersion of the biodegradable polymer in an organic solvent;

b. applying the dispersion on the surface of the implant; and c. evaporating the organic solvent.

21. The method of claim 20, wherein the steps of applying and evaporating occur at a temperature between 0 and 30° C. (32–86° F.).

22. The method of claim 20, wherein the the step of evaporating occurs in a gaseous atmosphere substantially saturated with a solvent vapor.

23. The method of claim 20, wherein steps b and c are repeated at least two times.

24. The method of claim 20, wherein the dispersion is a colloidal solution of the biodegradable polymer in the solvent.

25. The method of claim 24, wherein the colloidal solution is produced by allowing a mixture of polymer and solvent to stand for 1 minute to 24 hours.

26. The method of claim 24, wherein the colloidal solution is filtered prior to its application.

27. The method of claim 26, wherein the colloidal solution is filtered through a micropore filter with a pore size of 0.45 µm or smaller.

28. The method of claim 20, wherein the solvent is ethyl acetate or chloroform.

29. The method of claim 20, wherein the dispersion contains 20 to 300 mg of polymer per ml of solvent.

30. An implant for compensating for pathological changes in the spinal column or locomotor system, the implant comprising a surface and a body having a varnish-like coating of a thickness of 100 µm or less and made of a biodegradable polymer, wherein the implant comprises a base material which is not biodegradable; and the varnish-like coating forms an adhesive bond to the surface of the implant, and wherein said implant is made by:

a. preparing a dispersion of the biodegradable polymer in an organic solvent;

b. applying the dispersion on the surface of the implant; and c. evaporating the organic solvent.

31. The implant of claim 30, wherein the base material is a metal or an alloy.

32. The implant of claim 30, wherein said base material is stainless steel.

33. The implant of claim 30, wherein said base material is titanium.

34. An implant made by the method of claim 20.

* * * * *

UNITED STATES PATENT AND TRADEMARK OFFICE
CERTIFICATE OF CORRECTION

PATENT NO. : 6,998,134 B2
APPLICATION NO. : 09/801752
DATED : February 14, 2006
INVENTOR(S) : Schmidmaier et al.

Page 1 of 1

It is certified that error appears in the above-identified patent and that said Letters Patent is hereby corrected as shown below:

In claim 1, column 12, line 11, the term "solvent1" should read --solvent--;

In claim 12, column 12, line 42, the expression "by weight percentage" should read --weight percentage--; and In claim 22, column 13, line 14, the expression "the the step of" should read --the step of--.

Signed and Sealed this

First Day of August, 2006

JON W. DUDAS
*Director of the United States Patent and Trademark Office*